(12) United States Patent
Lee et al.

(10) Patent No.: US 6,520,934 B1
(45) Date of Patent: Feb. 18, 2003

(54) CATHETER ASSEMBLIES WITH FLEXIBLE RADIOPAQUE MARKER

(75) Inventors: Jeong S. Lee, Diamond Bar, CA (US); Vidya Nayak, Cupertino, CA (US); John Schreiner, Hemet, CA (US); Christine Gutting, Murrieta, CA (US); Edwin Wang, Tustin, CA (US); Gary Heinemann, Campbell, CA (US); Roseminda White, Wildomar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/474,668

(22) Filed: Dec. 29, 1999

(51) Int. Cl.⁷ .............................................. A61M 29/00
(52) U.S. Cl. ................................................ 604/103.1
(58) Field of Search .................... 604/103.1, 96.01, 604/95.01, 264, 93.01, 103.09, 100; 600/433–435, 466

(56) References Cited

U.S. PATENT DOCUMENTS

| | | | | |
|---|---|---|---|---|
| 4,323,071 A | | 4/1982 | Simpson et al. ............. 128/343 |
| 4,917,666 A | | 4/1990 | Solar et al. .................... 604/95 |
| 4,938,220 A | * | 7/1990 | Mueller, Jr. .................. 128/658 |
| 4,946,466 A | * | 8/1990 | Pinchuk et al. ............. 606/194 |
| 4,998,917 A | * | 3/1991 | Gaiser et al. ................. 604/96 |
| 5,147,318 A | * | 9/1992 | Hohn ........................... 604/174 |
| 5,171,232 A | | 12/1992 | Castillo et al. .............. 604/280 |
| 5,209,730 A | | 5/1993 | Sullivan ........................ 604/96 |
| 5,300,048 A | * | 4/1994 | Drewes, Jr. et al. ........ 604/280 |
| 5,395,332 A | * | 3/1995 | Ressemann et al. .......... 604/96 |
| 5,536,242 A | * | 7/1996 | Willard et al. ................ 604/30 |
| 5,547,472 A | | 8/1996 | Onishi et al. ................. 604/93 |
| 5,549,552 A | * | 8/1996 | Peters et al. .................. 604/96 |
| 5,558,652 A | | 9/1996 | Henke ......................... 604/280 |
| 5,591,129 A | * | 1/1997 | Shoup et al. .................. 604/96 |
| 5,606,981 A | | 3/1997 | Tartacower et al. ......... 128/772 |
| 5,669,932 A | | 9/1997 | Fischell et al. .............. 606/198 |
| 5,728,042 A | | 3/1998 | Schwager |
| 5,759,174 A | | 6/1998 | Fischell et al. ................ 604/96 |
| 5,779,731 A | | 7/1998 | Leavitt ........................ 606/194 |
| 5,823,995 A | * | 10/1998 | Fitzmaurice et al. .......... 604/96 |
| 5,836,892 A | | 11/1998 | Lorenzo ...................... 600/585 |
| 5,846,199 A | | 12/1998 | Hijlkema et al. ............ 600/435 |
| 5,865,721 A | | 2/1999 | Andrews et al. .............. 600/18 |
| 6,139,511 A | * | 10/2000 | Huter .......................... 600/585 |
| 6,165,196 A | * | 12/2000 | Stack et al. .................. 606/194 |

FOREIGN PATENT DOCUMENTS

| WO | WO 9713455 | 4/1997 |
|---|---|---|
| WO | WO 9748435 | 12/1997 |

* cited by examiner

*Primary Examiner*—Anhtuan T. Nguyen
*Assistant Examiner*—Ann Y. Lam
(74) *Attorney, Agent, or Firm*—Blakely, Sokoloff, Taylor & Zafman LLP

(57) ABSTRACT

A catheter assembly comprising a shaft and at least one flexible radiopaque marker affixed with the shaft. Flexibility of radiopaque marker is achieved by using a segmented band of radiopaque material or a coiled band formed by winding a wire or hollow tube filled with radiopaque material. The flexible radiopaque marker may be affixed with the shaft by an adhesive, by swaging, by crimping, by soldering, or by spring-action tension fit against the shaft.

4 Claims, 4 Drawing Sheets

CATHETER ASSEMBLIES WITH FLEXIBLE RADIOPAQUE MARKER

FIELD OF THE INVENTION

The present invention relates to medical devices in general and catheter assemblies having flexible radiopaque markers in particular.

BACKGROUND

Catheters have found widespread clinical use, for both diagnostic and interventional procedures. In performing, for example, intravascular catheter procedures, a physician typically uses a fluoroscope (e.g., an X-ray machine) to visualize a patient's vascular structure. To assist the physician in guiding and positioning the catheter within the patient's vascular system, catheters typically have one or more marker bands affixed to the shaft that are highly visible under the fluoroscope.

FIGS. 1A and 1B illustrate an example of a balloon catheter assembly and a marker band, respectively, from the prior art. The catheter assembly 10 comprises a shaft 15 and a balloon member 14 disposed around a distal section of the shaft 15. The balloon member 14 has a proximal portion 11 and a distal portion 13 and an inflatable portion 12 therebetween. The proximal portion 11 and the distal portion 13 of the balloon member are affixed to the shaft 15. The catheter assembly 10 depicted in FIG. 1A has a single marker band 19 positioned to indicate a midpoint of the inflatable portion 12 of the balloon member 14.

The marker band 19 is shown in an expanded view in FIG. 1B. The marker band 19 is a solid band of a radiopaque metal, such as gold, platinum, tungsten, iridium, etc. and alloys thereof. Typically, the marker band 19 is slipped around and onto the shaft 15 and then affixed to the shaft with an adhesive or by heating the shaft.

Vascular structures can be very tortuous, and marker bands of the prior art present an impediment to navigating the catheter through such tortuous anatomy, especially around a tight bend, because such marker bands are rigid and have no flexibility. The marker band's rigidity additionally present problems to passing the catheter through a lesion.

SUMMARY

The present invention provides catheter assemblies having at least one flexible radiopaque marker affixed with the shaft. In one embodiment of the present invention, the flexible radiopaque marker is a segmented band of a radiopaque material. The segmented band further has a longitudinal slit running from one end of the segmented band to the opposite end of the segmented band. In another embodiment, the flexible radiopaque marker comprises a coil of a radiopaque material. The radiopaque material may comprise a radiopaque metal. Alternatively, the radiopaque material may comprise a polymeric material loaded with a radiopaque agent.

DETAILED DESCRIPTION

The present invention will be described below in connection with the embodiments depicted in the figures. Neither the figures nor the descriptions below are intended to limit the present invention in any way. In particular, although the present invention will be described in the context of catheters and balloon catheter assemblies, the present invention may be used in conjunction with other types of medical devices, such as stents, sheaths, inflation devices, and the like, that are inserted into a body where visibility under a fluoroscope is desired.

In the following description, specific details are set forth to provide a thorough understanding of the present invention, however, it will be appreciated by those of ordinary skill in the art that the present invention may be practiced without these specific details. In other instances, details of well-known steps, structures and techniques have been omitted to avoid obscuring the present invention.

Figure 1A:
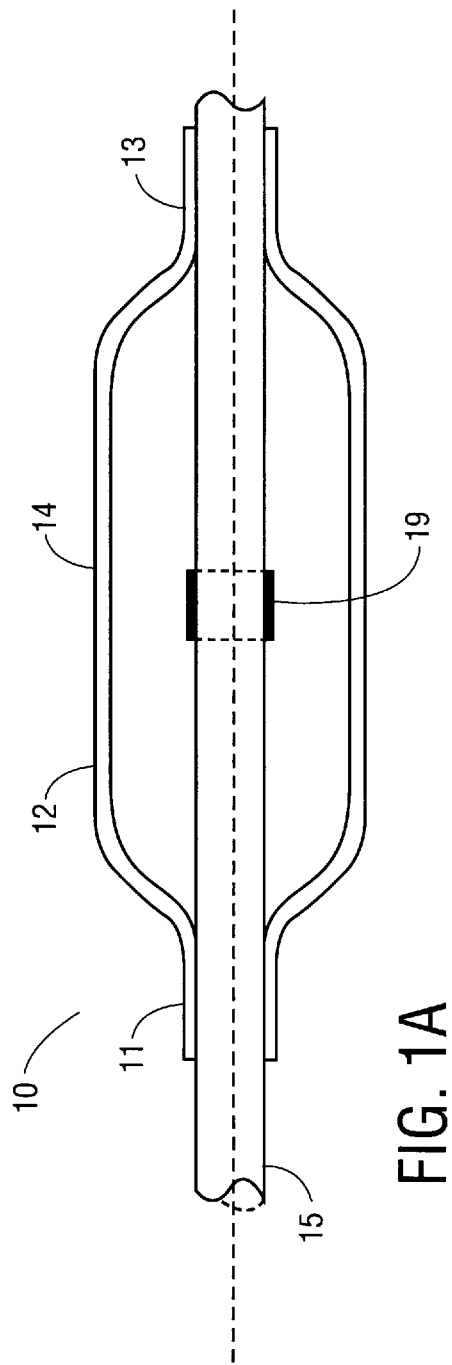
FIG. 1A is a cross-sectional view of a catheter assembly of the prior art having a single marker band.
Figure 1B:
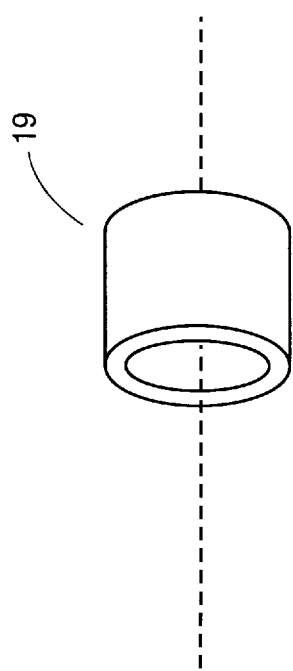
FIG. 1B shows an expanded view of a marker band of the prior art.
Figure 2:
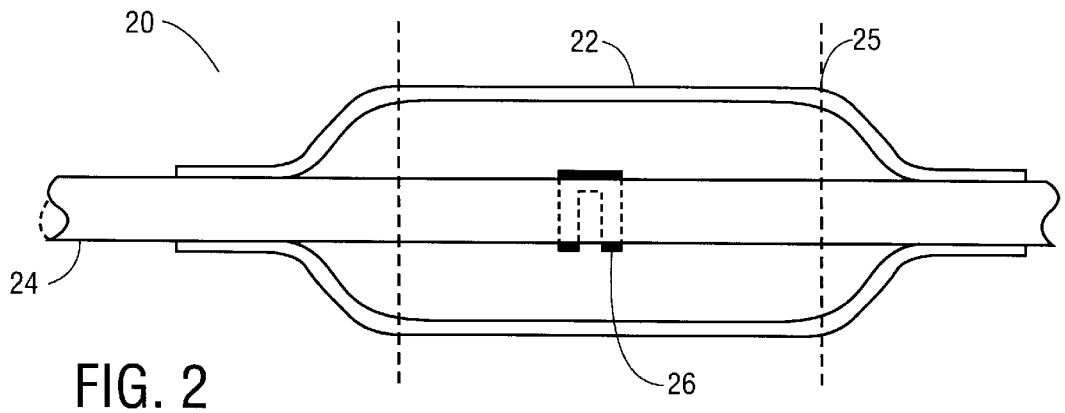
FIG. 2 is a cross-sectional view of one embodiment of a catheter assembly having a flexible radiopaque marker in accordance with the present invention.

FIG. 2 depicts one embodiment of a catheter assembly that incorporates a flexible radiopaque marker of the present invention. The catheter assembly 20 in depicted in FIG. 2 is similar to the catheter assembly 10 shown in FIG. 1. The catheter assembly 20 has a single flexible radiopaque marker 26 affixed on an outer surface of a shaft 24 and positioned so as to indicate the midpoint of an inflatable portion 22 of a balloon member 25.

Figure 3A:
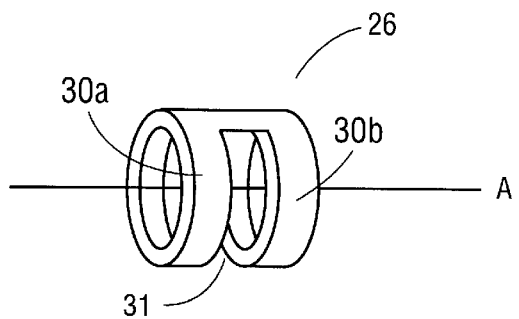
FIGS. 3A and 3B show expanded views of two embodiments of the flexible radiopaque marker in accordance with the present invention comprising a segmented band having two and three segments, respectively.

FIG. 3A shows an expanded view of the flexible radiopaque marker 26 from the catheter assembly 20 of FIG. 2. In this embodiment, the flexible radiopaque marker 26 comprises a band of a radiopaque material having one notch 31 formed transverse the longitudinal axis (A) of the band and that divides the band into two segments 30a, 30b. The two segments 30a, 30b can move relative to one another, allowing the flexible radiopaque marker 26 to bend more easily than the solid bands of the prior art.

Figure 3B:
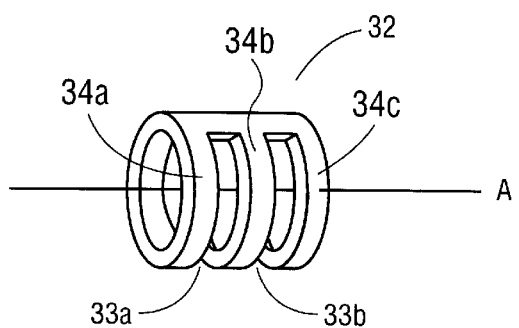

FIG. 3B depicts another embodiment of a flexible radiopaque marker of the present invention. In this embodiment, the flexible radiopaque marker 32 comprises a band of radiopaque material having two notches 33a and 33b formed transverse the longitudinal axis (A) thereof and that divide the band into three segments 34a, 34b, and 34c. As compared to the flexible radiopaque marker 26 shown in FIG. 3A, the flexible radiopaque marker 32 shown in FIG. 3B has an additional degree of freedom due to the additional segment and so has even greater flexibility.

Figures 4A, 4B:
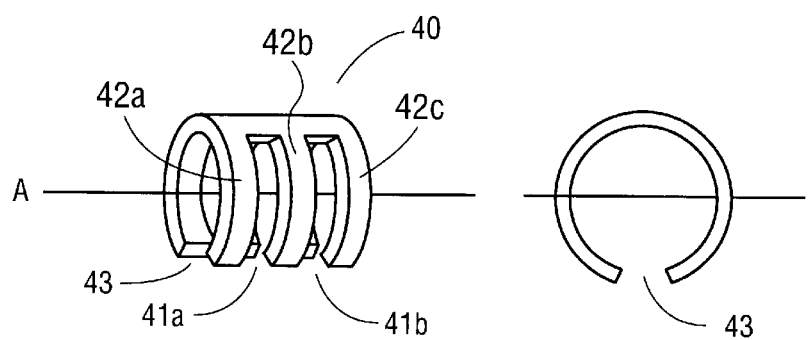
FIGS. 4A and 4B show expanded views from the side and front of a flexible radiopaque marker having a longitudinal slit in accordance with the present invention.
Figure 7:
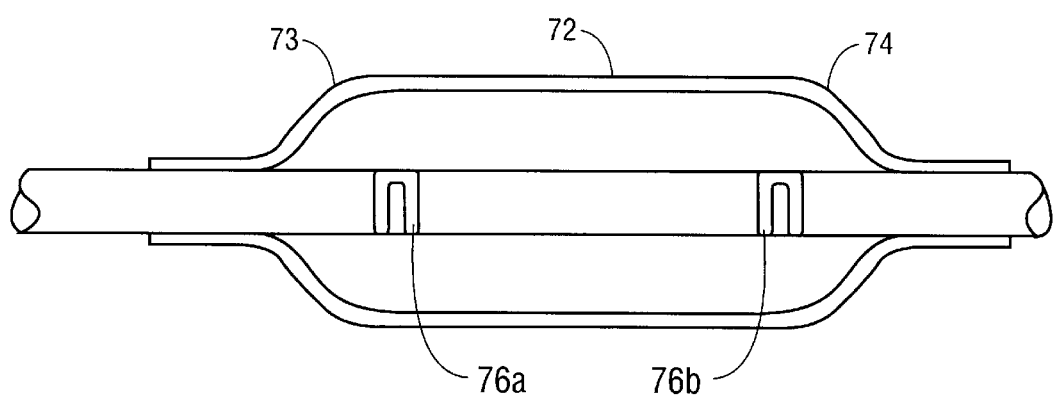
FIG. 7 shows one embodiment of a catheter assembly with two flexible markers affixed to an inner surface of a catheter shaft.

FIGS. 4A and 4B show two views of a variation on the type of flexible radiopaque marker illustrated by the embodiments shown in FIGS. 3A and 3B. The flexible radiopaque marker 40 shown in FIGS. 4A and 4B is similar to that shown in FIG. 3B, having two notches 41a and 41b and three segments 42a, 42b, and 42c. Additionally, the flexible radiopaque marker 40 has a longitudinal slit 43 running from one end of the flexible radiopaque marker to the other end of the flexible radiopaque marker. The longitudinal slit 43 allows the flexible radiopaque marker to be wrapped around and embedded in the catheter shaft, which allows the flexible radiopaque marker of the present invention to have a smaller diameter and hence smaller profile than the markers of the prior art that are slipped over the inner shaft.

The notches and slits may be formed using a variety of techniques known in the art, such as laser cutting and the like. One of skill in the art will recognize that the type of flexible radiopaque marker illustrated by the embodiments shown in FIGS. 3A–3B and 4A–4B may have as many notches and thus have as many segments as can be formed therein. The more segments, the more degrees of freedom and the greater the flexibility of the flexible radiopaque marker.

Figure 5:
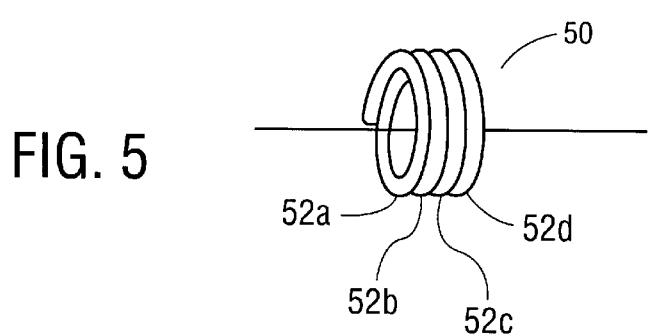
FIG. 5 shows an embodiment of the flexible radiopaque marker in accordance with the present invention comprising a coil having four segments.

FIG. 5 shows another embodiment of flexible radiopaque marker according to the present invention. In this embodiment, the flexible radiopaque marker 50 comprises a coil of radiopaque material. Each turn of the coil 52a, 52b, 52c, and 52d acts as a separate segment. In one embodiment, the coiled flexible radiopaque marker is made of a wire of radiopaque material. In another embodiment, the coiled flexible radiopaque marker is made of a hollow tube made of, e.g., stainless steel, gold, copper, silver, and the like, and filled with a radiopaque material. The wire or radiopaque filled tube may have an outer diameter of less than about 3 mils, typically about 2 mils.

The coiled flexible radiopaque marker may be made by winding or braiding the wire or radiopaque filled tube around a mandrel and then assembled with the catheter assembly, or by winding or braiding the wire or radiopaque-filled tube directly onto the catheter shaft. The radiopaque coil marker may be wound directly onto the catheter shaft under tension to form a flexible radiopaque marker that is embedded into the catheter shaft. The wire or radiopaque-filled tube may be wound continuously in one direction to form a continuous coil (as shown in FIG. 5), or may be wound back and forth in zigzag pattern around the mandrel or the shaft.

In still another embodiment, the coiled flexible radiopaque marker described above may be coated with a polymer layer, to keep the ends of the wire from fraying and the coil from unraveling. The polymer may be applied as a solution over the coil, or as a heat-shrink film that is wrapped around the coil. Typically, the polymer layer will be made of a soft polymer material, such as a low durometer polyurethane, polyamide-polyether block co-polymer (e.g., Pebax®), and the like.

The dimensions of the flexible radiopaque markers will depend upon the particular application and particular device to which the markers are affixed. For use with percutaneous transluminal coronary angioplasty (PTCA) devices, for example, flexible radiopaque markers that are affixed to the outer surface of the catheter shaft will have an outer diameter typically in the range of between about 22 mils and about 27 mils. For use with peripheral percutaneous transluminal angioplasty devices, the flexible radiopaque markers may have an outer diameter of up to about 50 mils.

Typically, radiopaque markers have an overall length between about 1 millimeter and about 3 millimeters. However, given the increased flexibility of flexible radiopaque markers according to the present invention, the flexible radiopaque marker may have a much larger overall length. The overall length of a flexible radiopaque marker according to the present invention may range between about 1 millimeter and about 50 millimeters.

Flexible radiopaque markers of the present invention may be affixed with the shaft by crimping, or by swaging, or with an adhesive, or by heating, or by soldering, or by the spring-action tension applied by the flexible radiopaque marker against the shaft, or by other means known in the art. When an adhesive is used, the adhesive is advantageously a flexible adhesive such as a silicone-based adhesive, urethane-based adhesive, cyanoacrylate-based adhesive, and the like.

Crimping, swaging and spring-action tension have the advantage of reducing the outer diameter of the markers, or allowing lower profile markers to be used, which would help facilitate the navigation of the catheter assembly through tortuous body lumens. It is noted that a longitudinal slit as shown in FIGS. 4A and 4B would facilitate (though is not necessary for) crimping, swaging or spring-action tension of the flexible radiopaque markers of the present invention.

The flexible radiopaque markers of the present invention are made of a radiopaque material. The radiopaque material may be a radiopaque metal, such as gold, platinum, iridium, tungsten, nickel, tantalum, iron, carbon, manganese, cobalt, alloys thereof, and the like. Alternatively, the radiopaque material may be a polymeric material with a radiopaque agent incorporated therein. The polymeric material advantageously provides further flexibility for the flexible radiopaque markers of the present invention.

Any polymeric material may be used. Some examples of polymeric materials that may be used in the present invention include polyurethanes, polyamides, polyimides, polyesters, polyethers, polyethylenes, polypropylenes, co-polymers thereof, and the like. The polymeric materials may be expanded under pressure and/or heat to facilitate assembly of the flexible radiopaque marker onto the catheter shaft. Any radiopaque agent may be used. Some examples of radiopaque agents that may be used in the present invention include barium, bismuth, tungsten, compounds thereof, and the like. In one embodiment, up to approximately 25% by volume of a radiopaque agent is incorporated into the polymeric material without detrimental effect in its mechanical properties. An example of a radiopaque material suitable for use in the present invention is a polyamide-polyether block co-polymer (e.g., Pebax®) having approximately 25% by volume of bismuth trioxide incorporated therein.

EXAMPLES

Two prototypical PTCA balloon catheter assemblies having flexible radiopaque markers formed in accordance with the present invention have been made. The PTCA balloon catheter assemblies had a 3×18 millimeter balloon on a tri-layer (Pebax®/Primacor® (ethylene acrylate acid)/high density polyethylene) shaft having an outer diameter of 20.5 mils.

Coiled flexible radiopaque markers were made from thin wires of a platinum-iridium (Pt/Ir) alloy and of a platinum-nickel (Pt/Ni) alloy having an outer diameter of 2 mils. The coiled flexible radiopaque markers were formed by winding the wire around a mandrel and then cut to have an overall length corresponding to the working length of the balloon member, i.e., 18 millimeters. The coiled radiopaque markers for these examples had an inner diameter of slightly larger than the outer diameter of the shaft, i.e., 21 mils. It is noted, however, that, given the spring action of the coil, coiled flexible radiopaque markers having an inner diameter approximately the same or slightly smaller than the outer diameter of the shaft may be used and assembled with catheter assemblies in a similar manner as described below.

In these examples, the catheter assemblies were assembled with the coiled radiopaque markers by first applying a thin layer of adhesive to the outer surface of the tri-layer shaft. Then the flexible radiopaque marker was slipped over the shaft and the layer of adhesive, and affixed via the adhesive with the outer surface of the shaft. The Pt/Ir flexible radiopaque marker was affixed using an ultraviolet cured adhesive and had an outer diameter of 27 mils (when assembled on the shaft). The Pt/Ni flexible radiopaque marker was affixed using a cyanoacrylate-based adhesive and had an outer diameter of 26 mils. The balloon member was then assembled over the shaft and centered over the flexible radiopaque markers.

The PTCA catheter assemblies with Pt/Ir and Pt/Ni flexible radiopaque markers as described above were observed to possess greater visibility and greater flexibility than similar catheter assemblies having solid marker bands of the same radiopaque materials.

Figure 6:
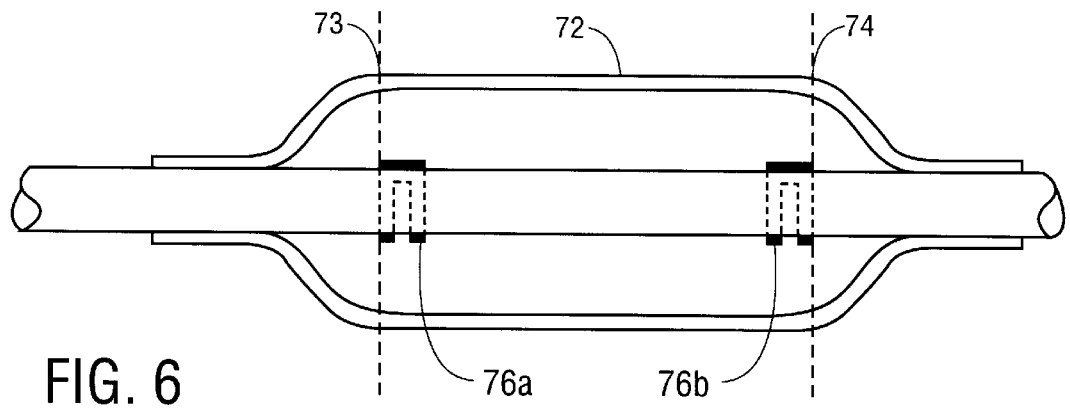
FIG. 6 shows one embodiment of a catheter assembly having two flexible radiopaque markers in accordance with the present invention.

Although the catheter assemblies described above incorporated only one flexible radiopaque marker, catheter assemblies of the present invention are not so limited. Catheter assemblies of the present invention can have more than one flexible radiopaque markers affixed with the shaft, in which case it would be advantageous to position the flexible radiopaque markers to indicate specific positions of interest on the catheter. For example, as shown in the embodiment with two flexible radiopaque markers depicted in FIG. 6, it is advantageous to position a first flexible radiopaque marker 76a to define a proximal end 73 of the inflatable portion 72 of the balloon member and a second flexible radiopaque marker 76b to define a distal end 75 of the inflatable portion 72.

Flexible radiopaque markers of the present invention may be affixed with (e.g., adhered with, embedded within or onto, crimped or swaged around, etc.) either an inner surface or an outer surface of the shaft, and may be used with any type of catheter assembly or any type of medical device where visibility under a fluoroscope is desired.

Those of ordinary skill in the art will understand that numerous other variations, modifications and improvements may be made to the embodiments and examples described above that still fall within the scope of the invention as claimed.

What is claimed is:

1. A catheter assembly comprising:

at least one segmented marker band comprising a radiopaque material, the segmented marker band having two ends and a longitudinal slit formed from one end of the segmented marker band to the other end of the segmented marker band; and a shaft having an inner surface and an outer surface, wherein the at least one segmented marker band being affixed on the inner surface.

2. A catheter assembly comprising:

at least one segmented marker band comprising radiopaque material, the segmented marker band having two ends and a longitudinal slit formed from one end of the segmented marker band to the other end of the segmented marker band; and a balloon member having a proximal portion, a distal portion, and an inflatable portion therebetween, wherein the at least one segmented marker band defines a midpoint of the inflatable portion.

3. A catheter assembly comprising:

at least one segmented marker band comprising radiopaque material, the segmented marker band having two ends and a longitudinal slit formed from one end of the segmented marker band to the other end of the segmented marker band; and a balloon member having a proximal portion, a distal portion, and an inflatable portion therebetween, wherein the at least one segmented marker band has a length corresponding to a working length of the balloon member.

4. A catheter assembly comprising:

two segmented marker bands comprising radiopaque material, each segmented marker band having two ends and a longitudinal slit formed from one end of the segmented marker band to the other end of the segmented marker band; and a balloon member having a proximal end, a distal end, and an inflatable portion therebetween, wherein one segmented marker band is positioned to indicate the proximal end and the other segmented marker band is positioned to indicate the distal end.

* * * * *